United States Patent [19]

Chang

[11] Patent Number: 4,652,257

[45] Date of Patent: Mar. 24, 1987

[54] MAGNETICALLY-LOCALIZABLE, POLYMERIZED LIPID VESICLES AND METHOD OF DISRUPTING SAME

[75] Inventor: Eddie L. Chang, Cheverly, Md.

[73] Assignee: The United States of America as represented by the Secretary of the Navy, Washington, D.C.

[21] Appl. No.: 714,411

[22] Filed: Mar. 21, 1985

[51] Int. Cl.$^4$ .............................................. A61M 31/00
[52] U.S. Cl. ........................................ 604/52; 128/1.3
[58] Field of Search ..................... 604/52, 51, 57, 65; 128/1.3, 1.1

[56] References Cited

U.S. PATENT DOCUMENTS 3,358,676 12/1967 Frei et al. .
4,005,699 2/1977 Bucalo .
4,247,406 1/1981 Widder et al. .
4,269,826 5/1981 Zimmerman et al. .
4,331,654 5/1982 Morris .
4,345,588 8/1982 Widder et al. .
4,590,922 5/1986 Gordon ............................ 128/1.3

Primary Examiner—John D. Yasko
Attorney, Agent, or Firm—Sol Sheinbein; Wendell R. Guffey

[57] ABSTRACT

Polymerizable lipids are used to encapsulate therapeutic agents and ferromagnetic particles into lipid vesicles. The vesicles are polymerized, injected into the body upstream of a targeted capillary bed, allowed to flow within the bloodstream to the targeted site, and held there by an externally applied magnetic field. The magnetic field is oscillated at sufficient periodicity to destabilize or disrupt the vesicle membrane thus effecting a controlled release of the therapeutic agent.

6 Claims, No Drawings

MAGNETICALLY-LOCALIZABLE, POLYMERIZED LIPID VESICLES AND METHOD OF DISRUPTING SAME

BACKGROUND OF THE INVENTION

This invention relates generally to vesicles and more particularly to polymerizable, lipid vesicles and the method of administering therapeutic agents therewith.

Used herein, "lipid vesicle" and "liposome" refer to a hollow, spherical like structure having an interior which can encapsulate aqueous solvents and their solutes; and having a shell or membrane composed of lipid layers. "Lipid microsphere" refers to a solid lipid spherical like structure such that any substance dissolved in the microsphere must generally be lipid soluble and, hence, hydrophobic or amphiphilic.

Typical methods of treating disease involve intravascular injections of fairly toxic therapeutic agents. To maximize the efficacy at the desired location, the blood plasma concentration of the therapeutic agent must be kept at a high level throughout the body. This approach produces undesirable side effects since the therapeutic agent acts upon many in vivo systems. Encapsulation of the therapeutic agent into lipid microspheres and targeting the microspheres to a specific release site within the body have been suggested to avoid many undesirable side effects caused by high blood plasma concentrations. The therapeutic agent is encapsulated into microspheres containing ferromagnetic embedded particles. The microspheres are injected into the body upstream of the target site, allowed to flow in the blood stream to the target site, and immobilized by an external magnetic field. The therapeutic agent leaks into the target site or is released by in vivo enzymatic action. This produces a high concentration of the therapeutic agent at the target site while keeping the overall concentration in the blood plasma low thereby minimizing undesirable side effects on the rest of the body.

There are, however, problems and limitations with this technique: only fat soluble therapeutic agents can be easily encapsulated in lipid microspheres and, after injection, the microspheres may be physically or chemically degraded before they reach the target site. Additionally, there is no effective means to control the rate of release of the therapeutic agent. Current methods rely on leakage of the therapeutic agent from the microsphere or on in vivo enzymatic activity that degrades the microsphere at an indeterminate rate.

U.S. Pat. No. 4,247,406 discloses a magnetically localizable, biodegradable microspheres formed from an amino acid polymer matrix embedded with magnetic particles. The microspheres were formed from matrix materials, such as albumin, which could be attacked in vivo by proteolytic enzymes thus releasing the microsphere's contents. To obtain slower release rates, enzymatic activity was inhibited by crosslinking the matrix using known hardening agents. No method of increasing the life time or stability of the vesicles was disclosed. The release rate for the microspheres' contents was dependent on the degree of crosslinking and the inherent proteolytic enzyme activity in vivo.

U.S. Pat. No. 4,345,588 discloses a method for immobilizing therapeutic agent carrying microsphere in a capillary bed using an 8000 gauss magnetic field following injection of the microspheres into an upstream artery and subsequent migration of the vesicles to the desired capillary bed. No method for releasing the therapeutic agent is disclosed. The microsphere used were formed from nonpolymerizable lipids using the techniques known in prior art. The therapeutic agent is carried by amino acid polymers which are hardened by denaturation of the protein or by hardening with formaldehyde.

U.S. Pat. No. 3,474,779 describes a method for administering therapeutic agents in which magnetic microspheres are intravascularly administered so that they pass into a capillary bed where they are caught by an applied magnetic field, and magnetically retained in the capillary bed until the therapeutic agent contained in the microsphere is released.

Microcapsules containing magnetic particles are disclosed in U.S. Pat. No. 2,971,916. The microcapsules of up to 150 micrometers in diameter are formed by coacervation, the capsules having walls of hardened organic colloid material enclosing an oily liquid containing a dispersion of magnetic powder.

U.S. Pat. No. 3,663,687 teaches the use of biodegradable microspheres for intravascular administration of therapeutic agents. The microspheres are dimensioned so that they will lodge in the capillaries where they can be degraded by enzymatic action thus releasing the therapeutic agent. The patent further teaches that the rate of release of the therepeutic agent can be varied by cross-linking the protein material forming the microspheres.

Lipids have been used to encapsulate therapeutic agents in an effort to selectively administer them to target sites. Rahman, *Proc. Soc. Exp. Biol. Med.*, 146, 1173 (1974), studied the effect of liposome encapsulated antinomycin D on tumors in mice and concluded that mean survival times for those mice treated with encapsulated therapeutic agents increased.

Gregoriades, *Biomedical and Biophysical Research Communications*, 65:537 (1975), studied the possibility of holding liposomes to targeted cells using liposomes containing anti-tumor drugs.

Sozka et al., *Am. Rev. Biophys. Bioeng.*, 9:467–508 (1980), reviews the known methods for producing and characterizing lipid vesicles. Dispersion, sonication, detergent solubilization and dialysis, solvent injection, reverse phase evaporation, extrusion, fusion and freeze/thaw techniques are typical methods used to produce lipid vesicles. A vesicle with desired size and stability characteristics can be produced using one or more of the above techniques in combination with various separating procedures such as column chromatography.

Thus, the prior art is lacking a rugged and stable means for transporting therapeutic agents to in vivo targeted sites. The vehicles used are subject to premature enzymatic attack and physical degradation. Additionally, current methods rely on timely enzymatic activity or leakage to release the encapsulated therapeutic agent at the targeted site. Neither method permits a controlled release of the therapeutic agent at the site.

SUMMARY OF INVENTION

It is, therefore, an object of this invention to provide lipid vesicles that are stable in vivo to unintended physical and chemical disruption.

A further object of this invention is to provide vesicles with polymerizable membranes.

A further object of this invention is to provide vesicles that can carry aqueous solutions of therapeutic agents.

A further object of this invention is to provide vesicles that can be immoblized at an in vivo target site by an external magnetic field.

A further object of this invention is to control the rate of release of an encapsulated therapeutic agent at the target site by oscillating the magnetic field.

These and other objects are achieved by encapsulating therapeutic agents and ferromagnetic particles in a lipid vesicle formed using polymerizable lipids which are subsequently polymerized to form a stable vesicle resistant to chemical and physical attack. The vesicles are attracted to the targeted site by an external magnetic field. Once localized at the target site, an oscillating magnetic field is used to destabilize the vesicle membrane resulting in controled release of the therapeutic agent at the target site.

Other objects, advantages, and novel features of the present invention will become apparent form the following detailed description of the invention.

DESCRIPTION OF THE INVENTION

The vesicles of this invention are characterized by a relatively impermeable lipid membrane that completely defines an enclosed volume which can contain solvents, solid particles, and solutes. In the preferred method of producing the vesicles, the solvent is evaporated from a mixture of lipids-polymerizable lipids in a rotary evaporator such that the lipids coat the inside surface of the rotary evaporator. A solution containing the therapeutic agent and the magnetic particles is added to the evaporator. The lipids are dispersed by vortexing the resulting mixture to get the lipids off the wall of the evaporator and into solution. The mixture is placed in a ultra-filtration cell and forced through polycarbonate membranes until vesicles having the desired size and membrane characteristics are produced. The vesicles should not exceed 5 micrometers in diameter and preferably measure less than 3 micrometers with an average of 1-2 micrometers. Also, the vesicles should have a unilamellar membrane which can be made more or less permeable by the motion of the encapsulated magnetic particles. The vesicles containing the encapsulated material and separated from the nonencapsulated material by column chromatography and polymerized using Ultraviolet Light.

The lipids used to form the vesicles are most commonly phospholipids, single-chain amphiphiles, or lysophosphatides, phospholipids being the preferred group. These include lipids with polymerizable moieties, the preferred group being unsaturated phospholipids containing, for example, diacetylene, butadiene, methacryloyl, or other similar moieties. Particular examples include bis [1,2-(methacryloyloxy) dodecanoyl]-L-alpha-phosphatidylcholine, a 16 carbon dimethacrylate phospholipid, and 1,2-bis(10,12-tricosadiynoyl)-sn-glycero-3-phosphocholine, a 23 carbon diacetylene phospholipid. The lipids should have branched or linear, unsubstituted aliphatic chains containing between eight and thirty carbon atoms, the preferred group having between 14 and 24 carbon atoms. Non-polymerizable lipids useful in practicing the invention include phospholipids such as phosphatidylcholine, phosphatidylserine, sphingomyelin or cardiolipin.

The magnetic particles which are to be encapsulated in the vesicle can be any ferromagnetic substance, preferably mono-domain size magnets from magnetic sensing bacteria, magnetites, ferrites or simply very fine iron filings, particularly ferrite particles having a particle size not exceeding 1000 angstroms, preferably between 100 and 500 angstroms.

Additives useful in preparing the vesicles include hydrophobic entities such as cholesterol, dicetylphosphate, or short chain lysolecithins, preferably cholesterol.

Surfactants useful in preparing the present invention include anionic agents such as sodium dodecylsulfate, cationic surfactants such as dialkyldimethylammonium hydroxide, and nonionic surfactants such as polyoxyethylene sorbitan monooleate. Naturally occurring surfactants such as lysolecithins are also useable. The precise nature of the surfacant is not critical to the practice of the invention.

The vesicles can be made using dispersion, sonication, detergent solubilization and dialysis, solvent injection, reverse phase evaporation, French press extrusion through filters, fusion and freeze/thaw techniques, preferably extrusion through polycarbonate filters. The method chosen to form the vesicles can affect the size of the vesicles. With some methods it may be necessary to use the extrusion process to reduce the size of larger vesicles. Additionally, the size of the vesicles useful in the present method can be controlled by taking only the fraction from the chromatography column which contains the desired size range.

The invention having been generally described, the following examples are given as particular embodiments of the invention and to demonstrate the practice and advantages thereof. It is understood that the examples are given by way of illustration and are not intended to limit the specification or the claims to follow in any manner.

The following are specific examples of the preparation of magnetically-localizable lipid vesicles according to the present invention.

EXAMPLE I

The vesicles can be made by removing the solvent with a rotary evaporator from a 75 micromole mixture of bis [1,2-(methacryloyloxy) dodecanoyl]-L-alpha-phosphatidylcholine, cholesterol, and dicetylphosphate (DCP) 5:4:1. 75 micromoles of the therapeutic agent and 110 mg of ferrite should be added to the lipid, which is dispersed by vortexing. The mixture is placed at 20° C. in an Amicon model 12 ultrafiltration cell and forced by argon pressure through polycarbonate membranes twice each through membranes with 6000 angstrom, 4000 angstrom, and 2000 angstrom pores. The resulting mixture of vesicles and non-encapsulated materials is separated at 4° C. on a column of Sepharose CL-6B. The purified vesicles should be concentrated on an $M_r$ 100000 cut-off ultrafilter, or by centrifugation at 5000 rev/min for 20 minutes.

EXAMPLE II

The procedure for preparing the vesicles is identical to that of Example I except no dicetylphosphate or cholesterol is used.

EXAMPLE III

The vesicles are fomed by identical prodedure to Example I except that dimyristoyl phosphatidylserine, a charged phospholipid is used instead of dicetylphosphate. The ratio of the lipids are kept the same.

EXAMPLE IV

The procedure followed Example I except Dimyristoyl phosphatidylcholine used in place of bis [1, 2-(methacryloyloxy) dodecanoyl] L-alpha-phosphatidylcholine. The extrusion temperature is around 22° C.

EXAMPLE V

Liposomes were prepared as in Example I except monodomain magnets from magnetic sensing bacteria is the magnetic substance used.

In the present invention, the vesicles are formed using polymerizable lipids which are subsequently polymerized by exposing the vesicles to ultra-violet light. Using a Rayonet Photochemical Reactor Chamber (model RPR-100), it takes between 5-30 minutes at a UV strength of about 25 watts. Alternatively, the vesicles can be formed from lipid/polymerizable lipid mixtures so as to vary the permability of the vesicle membrane. Once formed, the vesicles, containing the therapeutic agent and ferromagnetic particles, can be injected upstream from the target site. The vesicles migrate through the blood stream to the target area where they can be immobilized by an 8000 gauss magnetic field. Once immobilized, the vesicle's contents can be released by oscillating the magnetic field at a rate sufficient to vibrate the embedded ferromagnetic particles. The total contents of the vesicle can be released by oscillating the magnetic field sufficiently to lyse the membrane. Alternatively, particularly with the mixed lipid/polymerizable lipid vesicle, the contents can be released at a controlled rate by varying the oscillation rate so as to destabilize the membrane making it more permeable to the therapeutic agent but not so as rupture the membrane.

The magnetic field can be oscillated at a rate between 10 and 1200 cycles per second but a range between 500 and 1000 cycles per second is prefered.

The magnetic field can have any strength necessary to immobilize the vesicles. A range between 5000 and 12000 Gauss is prefered with 7000 to 9000 Gauss being most preferred.

For example, vesicles containing oncolytic agents could be injected intra-arterially upstream from a tumor, localized in the tumor by the magnetic field, and disrupted by oscillating the magnetic field. The toxicity of the oncolytic agents is, therefore, confined to the area where the tumor is located.

Therapeutic agents which can be encapsulated in the vesicles include hydrophillic materials such as vindesine sulfate, fluorouracil, antinomycin D, and the like. Basically, any known oncolytic agent, anti-inflamatory agent, anti-arthritic agent or similar agent which is hydrophillic can be incorporated into the vesicles.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method of delivering a therapuetic agent to a target site within the body, comprising the steps of:
   introducing ferromagnetic particle embedded vesicles containing said therapuetic agent into the blood stream upstream of said target site;
   applying a magnetic field having sufficient strength to immobilize said vesicles at said target site;
   immobilizing said vesicles at said target site; and
   oscillating said magnetic field at a rate sufficient to vibrate said ferromagnetic particles such that said vesicles's membrane is destabilized or lysed thereby controlling the rate of release of said therapuetic agent at said target site.

2. The method of claim 1 wherein said ferromagnetic particles are selected from the group consisting of monodomain size magnets from magnetic sensing bacteria, magnetics, ferrites, and fine iron filings, having a average particle size between 100 and 500 angstroms.

3. The method of claim 2 wherein said magnetic field is about 5000–12000 Gauss.

4. The method of claim 3 wherein said magnetic field is about 7000–9000 Gauss.

5. The method of claim 4 wherein said oscillation rate is about 10–1500 Hertz.

6. The method of claim 5 wherein said oscillation rate is about 500–1000 Hertz.

* * * * *